United States Patent [19]

Blank

[11] 4,018,594

[45] Apr. 19, 1977

[54] SUSTAINED RELEASE POLYMERS

[75] Inventor: Izhak Blank, Haifa, Israel

[73] Assignee: Hydrophilics International, Inc., New York, N.Y.

[22] Filed: Feb. 6, 1975

[21] Appl. No.: 547,488

Related U.S. Application Data

[63] Continuation-in-part of Ser. No. 279,888, Aug. 11, 1972, Pat. No. 3,959,237.

[30] Foreign Application Priority Data

Aug. 12, 1971 United Kingdom ............ 37936/71

[52] U.S. Cl. ...................... 71/97; 71/65; 71/79; 71/DIG. 1
[51] Int. Cl.² .......................... A01N 9/00
[58] Field of Search ............ 71/DIG. 1, 79, 97, 65; 424/81

[56] References Cited

UNITED STATES PATENTS

| | | | |
|---|---|---|---|
| 2,652,323 | 9/1953 | Mowry et al. ......................... 71/65 |
| 3,248,288 | 4/1966 | Wilder et al. ......................... 424/83 |
| 3,299,566 | 1/1967 | MacMullen ..................... 71/DIG. 1 |
| 3,576,760 | 4/1971 | Gould et al. ......................... 424/81 |
| 3,577,517 | 5/1971 | Kubot et al. ......................... 424/81 |
| 3,598,565 | 8/1971 | Graves ............................. 71/DIG. 1 |
| 3,779,952 | 12/1973 | Leonard, Jr. ................... 260/2.5 R |

FOREIGN PATENTS OR APPLICATIONS 898,915  6/1962  United Kingdom ............ 71/DIG. 1

*Primary Examiner*—Glennon H. Hollrah
*Attorney, Agent, or Firm*—McAulay, Fields, Fisher & Goldstein

[57] ABSTRACT

A composition comprising a copolymer of from 20 to 60 parts of at least one member selected from the class consisting of acrylic and methacrylic acids, from 20 to 70 parts of one member selected from the class of lower alkyl acrylates and lower alkyl methacrylates, and from 5 to 20 parts of a plasticizing monomer, in which at least some of the acid groups have been neutralized by multivalent cations, where a chemical, exclusive of water and plasticizer, releasable from a film of the referenced copolymer, is formed by casting and drying an aqueous solution of the copolymer containing the chemical.

5 Claims, No Drawings

SUSTAINED RELEASE POLYMERS

RELATION TO CO-PENDING APPLICATIONS

This application is a continuation-in-part of application Ser. No. 279,888, filed Aug. 11, 1972 now U.S. Pat. No. 3,959,237, in the name of Izhak Blank, for "Sustained Release Polymers." Said application was based upon British application Ser. No. 37936/71, filed Aug. 12, 1971.

BACKGROUND OF THE INVENTION

There are many situations where it is desired to provide a chemical compound at a locus over a prolonged period. However, if the compound is applied to the locus in pure form or in the presence of one of the conventional carriers it will normally only be present for a short while before ambient conditions disperse it or, if any sustained action is to occur, it has to be present in such large quantities initially that dispersion of ambient conditions takes a long time.

For example agricultural fine chemicals are generally applied by spraying in the form of an aqueous dispersion or by dusting onto plants or soil surrounding the plants. The result of these methods is that if sufficient active compound is applied to be present for a long period of time a substantial part of the chemical supplied will, during this time, be swept away by ambient conditions, such as wind, rain and surface water and part may be degraded by the action of sunlight. The fine chemicals act as pollutants in most cases, as also may their degradation products, and conventional methods of application tend to result in the use of much greater quantities than are actually required for the desire active effect.

One previous attempt at reducing the losses of fine chemicals in agriculture and elsewhere involves applying them in the form of granules or by applying them in the form of capsules, the chemicals being encapsulated within the polymeric material. Another proposal (in U.S. Pat. No. 2,652,322) has involved application of the fine chemicals in the presence of a hydroxyalkyl acrylate and another proposal has involved the use of copolymers of acrylic acid and acrylate as carrier. However none of these proposals is very satisfactory in that the fine chemical is usually released from the deposited film at an uncontrollable and rather fast rate.

It has been my object to devise new polymeric materials that are of particular value in the formulation of carriers that will result in sustained release of chemicals carried by the carriers, for example agricultural fine chemicals, and a further object has been the provision of compositions comprising agricultural fine chemicals and a carrier which is such as to permit sustained release of the fine chemicals, and a further object has been the provision of agricultural methods in which fine chemicals are released gradually.

New copolymers according to the invention are water soluble and are derived from a monomer mixture comprising 20 to 60 parts acrylic acid or methacrylic acid, 20 to 70 parts lower alkyl ($C_1$–$C_4$) acrylate or methacrylate, and 5 to 20 parts of a plasticizing monomer and are at least partially neutralized. In this specification all parts and percentages are by volume unless otherwise specified.

The amount of acid in the monomer mixture is usually at least 25 parts and often it is at least 40 parts and is preferably about 50 parts (e.g. 48 to 52 parts). The amount of alkyl acrylate or methacrylate is usually at least 25 parts and is often less than 50 parts.

A particularly preferred copolymer comprises 40 to 60 parts, preferably about 50 parts, acrylic acid or methacrylic acid, 25 to 50 parts, preferably 25 to 35 parts, alkyl acrylate or methacrylate and 5 to 20 parts, preferably 10 to 15 parts, of a plasticizing monomer and is at least partially neutralized.

The alkyl acrylate or methacrylate is usually methyl acrylate or methacrylate, most preferably methylmethacrylate. The acid is usually acrylic acid. The plasticizing monomer is preferably a long chain ester (e.g. having 8 to 18 carbon atoms in the chain) of acrylic acid or methacrylic acid, usually having an alkyl ester of, preferably, acrylic acid. A preferred ester is ethylhexylacrylate. Others include lauryl acrylate or methacrylate, stearyl acrylate or methacrylate and similar materials.

The copolymer may be derived from a monomer mixture containing other monomers, although usually such other monomers do not form a major proportion of the mixture. Preferably such other monomers are present in small amounts only, for example less than 10 parts. An example of a suitable other monomer is a cross-linking monomer, i.e. a monomer that will give rise to cross-linking within the copolymer. Cross-linking monomers which can be used include glycol dimethylacrylate and other diacrylates or dimethylacrylates, allyl methacrylate and divinylbenzene. The amount of cross-linking monomer is generally from 0.05 to 5 parts per 100 parts copolymer.

The copolymers of the invention may have high molecular weight, for example more than 1,000,000, and often more than 2,000,000, or even of the order of 4,000,000 or more. Such a high molecular weight can most easily be determined by measuring the intrinsic viscosity, and these high molecular weight copolymers have an intrinsic viscosity in methylethyl ketone at 25° C of 2.5 or more. However for some applications polymers with an intrinsic viscosity of as low as 0.6 or less can be used.

The copolymers can be made by any convenient method, for example emulsion, suspension or solution polymerisation, but the most satisfactory way of making the copolymers is by bulk copolymerisation. This gives a high molecular weight. The bulk polymerisation may be carried out at a temperature of from 40° to 60° C, preferably 45° to 5° C, usually in the presence of a suitable catalyst such as a peroxide, for example benzoyl peroxide or lauryl peroxide, or an azo compound, the preferred catalyst being $\alpha,\alpha$-azodiisobutyronitrile The polymerisation can also be catalysed by ultra violet radiation. When catalyst is added the amount may be from 0.01 to 0.12% by weight based on the total weight of monomers, the preferred amount being 0.03 to 0.05%. Polymerisation may be conducted in a casting cell.

If desired a chain terminator or regulator may be included in the reaction mixture in order to control the molecular weight. A suitable regulator is dodecanthiol.

The copolymers of the invention are water soluble as a result of neutralising some at least of the acidic groups with a suitable base. The corresponding compounds in which all the acidic groups are in the acid form are usually water insoluble. The partially or completely neutralised copolymers may be isolated as, for example, solid salts or as aqueous solutions.

A particular advantage of the copolymers of the invention is that, in addition to some of them being capable of giving very good sustained release of chemicals formulated with them, it is possible easily to vary the properties of a copolymer either during its production or after its production. Thus during its production the properties of a copolymer can be varied by appropriate selection of the starting monomers, and in particular the amount of acid, cross-linking agent and chain terminater if present. More important, however, is the ability to modify the properties of the copolymer after its formation. Thus the rate of release of chemicals from a film of the copolymer that carries them can be closely regulated by appropriate choice of neutralising agent and the amount of neutralising agent. Thus for any particular copolymer the polymer is most hydrophilic, and therefore most able to release chemicals carried by it quickly, if all the acidic groups are neutralised by a monovalent base. In order to control the rate of release it is therefore often preferred that only a proportion of the acid groups should be neutralised, for example between 25 and 90%, often 25 to 75%, of the acid groups.

A particularly preferred way of modifying the properties of the acidic copolymer is to neutralise it completely or partially with multivalent, usually divalent, organic or inorganic cations. The use of a multivalent base results in a form of cross-linking occurring between the acidic groups. For example instead of using a monovalent base, such as an alkali metal or ethanolamine, salts can be formed with metals such as zinc and copper. The most satisfactory way of forming these salts is to react the acidic copolymer with a zinc ammonium, copper ammonium or similar compound. An example of a suitable organic divalent base is ethylene diamine or ethylene imine.

The internally plasticised copolymer of the invention may additionally be externally plasticised by compounding it with conventional plasticisers such as dioctyl phthalate, dibutyl phthalate, or sebacates.

A releasable chemical can be released at a controlled rate at a selected locus if it is applied to the locus in the form of a composition with one of the described partially or completely neutralised copolymers. Copolymers may be neutralised with monovalent bases but for many uses, e.g. when the composition is being used agriculturally and rain falls, these may permit too rapid release of the releasable chemical. Copolymers neutralised with divalent bases generally give more gradual release since it is easily possible so to formulate them that the film obtained on drying the aqueous solution of the composition is of decreased solubility.

Accordingly preferred compositions according to the invention comprises a releasable chemical and a described copolymer that is partially or completely neutralised by a multivalent bases, as described. Naturally the releasable chemical is in addition to any water and any external plasticiser that may be present in the composition and is a chemical that is releasable from a film obtainable upon casting and drying aqueous composition. These releasable chemicals are usually agricultural fine chemicals but may be medicinal fine chemicals or others.

The preferred compositions are compositions containing agricultural fine chemicals.

Agricultural fine chemicals may be defined as pesticides, i.e. compounds for controlling or eliminating growth of undesirable organisms, for example the chemicals described variously as herbicides, nematocides, insecticides, fungicides, bactericides and biocides, and chemicals for regulating or promoting growth as a result of the application of extremely small quantities, for example the materials known as growth hormones, or nutrients containing trace elements. The invention is, of course, not intended for the application of large quantities of conventional bulk fertilisers. Examples of suitable fine chemicals include 4-thiazolyl benzimidazole, manganese ethylene bisdithiocarbamide, methyl-1-(butylcarbamoyl)-2-benzimidazole carbamate, 2,6-dichlorothiobenzamide and gibberellic acid.

The preferred compositions may be formed by compounding an agricultural fine chemical with a carrier that either includes the copolymer either in partially or completely neutralised state or includes both the copolymer in acidic form and an appropriate amount of a suitable base. The compositions may be solid or they may be liquid. Thus they may be solutions or dispersions of the agricultural fine chemical in an aqueous solution of the wholly or partially neutralised polymer. The compositions may contain conventional ingredients such as wetting agents.

The agricultural compositions may be applied by spraying, dipping, painting or any other suitable method of application either direct to plants, leaves, fruits, seeds, roots or parts thereof or indirectly for example to the soil surrounding growing plants.

The invention is of particular value for the application of herbicides. Most herbicides are water-soluble in various degrees and are eluted into the soil by the solubilising action of rain or irrigation water. The weedkillers are often also noxious to the plants to be protected and it is most desirable that they should be concentrated in the upper layer of the soil and that they should not be allowed to penetrate to such a depth that they come in contact with the roots of the crop.

We have now found that by applying the weedkiller in accordance with the invention a film can be formed on the top layer of the soil which retains the weedkiller and considerably reduces its leaching into the lower layers of the soil.

As a corollary, the fact that the weedkiller is limited to a narrower layer, makes its use safer for the crop, and smaller amounts can be used to achieve the same results.

For this application we have found that the most suitable copolymers are those having an extremely high molecular weight. We have also found that in order to obtain the best results, the copolymer obtained should be neutralised in such a way that the film obtained from its aqueous solution should have a much reduced solubility on drying. A zinc-ammonium complex or similar bases are very satisfactory.

We find generally that best results are obtained in agricultural methods when the copolymer is one of the very high molecular weight copolymers described above, for example formed by bulk polymerisation. The high molecular weight appears to give the film formed from the solution of the polymer good stability against degradation by ultra violet light and also renders the copolymer inherently very hydrophobic. Accordingly the copolymer can, and indeed must, contain a large amount of acid groups in order to render it sufficiently water soluble, and the presence of this large proportion in a hydrophobic structure makes it possible to control accurately the balance between the hydrophilic and hydrophobic properties in order to obtain optimum release rates and other properties.

The invention is illustrated in the following examples in which parts are by volume unless otherwise specified.

EXAMPLE 1

A copolymer was formed in a casting cell from a mixture of 35 parts methylmethacrylate, 54 parts acrylic acid and 10 parts ethylhexylacrylate and 1 part dodecanthiol. To this was added 500 p.p.m. of $\alpha,\alpha'$-azodiisobutyronitrile. The polymerisation was controlled at 45° to 55° C over a period of 24 hours but during the last three hours the temperature was raised to 80° C. This copolymer was termed copolymer A. It was ground to −200 mesh.

EXAMPLE 2

Another copolymer, copolymer B, was made by reacting by the method described in Example 1 a monomer mixture of 29 parts acrylic acid, 60 parts methylmethacrylate and 10 parts 2-ethylhexylacrylate and 1 part dodecanthiol with 500 p.p.m. $\alpha,\alpha'$-azodiisobutyronitrile. It was then ground as in Example 1.

EXAMPLE 3

A 2.5% aqueous solution of copolymer A was prepared by mixing, vigorously, the powdered polymer with water and adding sufficient sodium hydroxide to neutralise 36% of the carboxylic groups (sodium copolymer A). Sufficient 2,6-dichlorothiobenzamide powder was dispersed in the sodium copolymer A to obtain a weed killer to polymer ratio of 16:100.

A quantity of 2 milliliters of the dispersion was cast on a glass plate having an area of 10 centimeters by 4 centimeters so as to obtain a uniform film and the material was allowed to dry at room temperature. The film was then immersed in water, allowed to dry for 24 hours, and immersed again. The content of active material in the water after each immersion was determined by spectrophotometry. Thirteen total immersions were necessary to release all the active material from the polymeric film when the immersion time was 30 seconds, while only seven immersions were required with a 60 second immersion time. The amount of active material released during each immersion was essentially constant.

EXAMPLE 4

The same procedure was followed as in Example 3 except that the active material employed was 4-thiazolyl benzimidazole. The active material was released after eleven immersions in 30 seconds duration or seven immersions of 60 seconds duration.

EXAMPLE 5

The same procedure was followed as in Example 3 except that the active material was manganese ethylene bis dithiocarbamide. Complete exhaustion of the active material was obtained after ten immersions of 30 seconds or six immersions of 60 seconds.

EXAMPLE 6

Copolymer A was neutralised using a zinc ammonium complex in an amount sufficient to neutralise 36% of the carboxylic acid groups present (zinc copolymer A). On drying, the film lost ammonia and the zinc produced cross-linking drastically reducing the release rate. The release rate was diminished to such a degree that none of the active material was released during short immersion times.

A mixture of the sodium copolymer A and zinc copolymer A in a ratio of 1:1 was used in the same manner as in Example 1 with 2,6-dichlorothiobenzamide as the active material. Only 30% of the active material had been released from the copolymer mixture after 12–30 second immersions. Twelve immersions of 60 seconds duration resulted in the release of 45% of the active material while only eight immersions were required to release all of the active material when the immersions were of 120 seconds duration.

EXAMPLE 7

The same procedure was employed as in Example 6 but employing 4-thiazolyl benzimidazole as the active material. A negligible release was attained employing 30 second immersions. Twelve immersions of 60 seconds duration resulted in the released of 8% of the active material, while 20% of the active material was released employing 12 immersions of 120 seconds each.

EXAMPLE 8

The procedure of Example 3 was employed using zinc copolymer A in conjunction with 2,6-dichlorothiobenzamide. 90% of the active material was released after one 30 minute immersion.

EXAMPLE 9

The same procedure was followed as in Example 3 employing copolymer B with 33% of the carboxylic groups neutralised with zinc. The active material employed was 2,6-dichlorothiobenzamide. 40% of the active material was released after one 30 minute immersions, and 95% of the active material was released after one 60 minute immersion.

EXAMPLE 10

Copolymer B was completely neutralised with zinc employing a zinc ammonium complex. The active material employed following the procedure of Example 3, was 2,6-dichlorothiobenzamide. The amounts of active material released following controlled immersion times, were as follows:

| Time of Immersion (Minutes) | Active Material Released (%) |
| --- | --- |
| 30 | 11 |
| 60 | 50 |
| 120 | 72 |

EXAMPLE 11

Sodium copolymer A was used in conjunction with gibberilic acid in the manner described in Example 3. Approximately 5% of the active material was released during a 60 second immersion.

EXAMPLE 12

A copolymer prepared employing 25% acrylic acid, 65% methyl methacrylate, and 2-ethylhexyl acrylate by emulsion polymerisation. This copolymer was partially neutralised with sodium hyroxide and diluted with a 2.5% concentration. A quantity of 2,6-dichlorothiobenzamide was added to the copolymer solution and a film was formed as described in Example 3. After four 30 second immersions 25% of the active material was released, while 60% was released after four 60 second immersions.

EXAMPLE 13

Cucumber plants were infected with powdery mildew and then treated with agricultural chemicals to overcome the infection. The active ingredient employed was methyl-1-(butylcarbamoyl)-2-benzimidazol carbamate, in one case alone, and in the other case contained in a quantity of copolymer A of Example 1 completely neutralise with ammonia. Testing showed that the mixtures of the agricultural chemical with the hydrophilic copolymer was 10 times more effective than the agricultural chemical alone.

EXAMPLE 14

In a Sigma Blade Mixer were put 500 grams of copolymer A powder A powder prepared as per Example 1. Added 56 grams of sodium hyroxide in 40 grams of water. Mixed for 6 hours. The powder obtained was water soluble.

EXAMPLE 15

In a Sigma Blade Mixer were put 360 grams of copolymer A powder prepared as per Example 1. Added 30 grams of zinc oxide and mixed. Separately a mixture of 38 grams zinc oxide, 68 grams ammonium carbonate and 48 grams ammonia solution (28% concentration) was prepared. This second mixture was slowly added to the first. After completing the mixture, the whole was ground in a hammer mill to a fine powder, termed product X.

EXAMPLE 16

The powder obtained as per Example 15 was mixed with Methomyl (Lanate) in the proportion of 8 parts of Methomyl to 250 parts of the powder. This mixture was then dissolved in water to obtain a concentration of 0.08% of the toxicant.

Tests were carried out by spraying this solution on tomato plants and comparing it with a commercial formulation of the same toxicant at the same concentration. The Lanate-polymer combination still gave a mortality of 53% of the insects after 19 days, while the Lanate commercial formulation gave no mortality after this period.

EXAMPLE 17

The powder obtained as per Example 15 was mixed with methyl parathion in the proportion of 12.5 parts of powder to one part of methyl parathion. Tomato plants were sprayed with a solution of this mixture containing 0.1% of the toxicant. Locust was used as the test insect. The plants were subjected to intermittent rains of 10mm each.

Comparison was made with a commercial emulsifiable concentrated formulation of methyl parathion, using the same conditions and concentrations.

After 45 days and 13 rains the polymer-methyl parathion combination gave a kill of 73% of the insects, while the commercial formulation killed only 7% of the insects after 17 days and 5 rains.

EXAMPLE 18

In a laboratory ball mill 10 grams of copolymer A were mixed with a mixture comprising:

| | |
|---|---|
| $CuCo_3$ | 2.5 grams |
| $NH_4OH$ (28%) | 1.5 grams |
| $(NH_3)_2CO_3$ | 3.3 grams |

After 3 hours of mixing, a blue water-soluble powder was obtained.

EXAMPLE 19

The powder obtained as per Example 18 was mixed with Maneb in the proportion of 5 parts of polymer to one part of the fungicide. A solution of this mixture was prepared, containing 0.5% of Manb. For comparison, a commercial preparation of Maneb was used at the same concentration. The test was made on tomato leaves infected with curvularia. Discs were cut and inhibition zones were measured. The polymer-fungicide combination gave an inhibition zone of 20mm diameter after 14 days, while the commercial Maneb formulation gave an inhibition zone of only 3mm diameter after 4 days.

EXAMPLE 20

The powder obtained as per Example 14 was mixed with methyl parathion in the proportion of 25 parts of powder to 2 parts of methyl parathion. An aqueous solution was prepared from this mixture, containing 0.2% methyl parathion. Comparison was made with commercial methyl parathion EC at the same concentration. Tests were made on tomato plants, using laphygma exigua as the test insect.

The polymer-toxicant combination still gave 100% kill after 24 days, while the commercial formulation gave 57% kill after 5 days and no kill after 8 days.

EXAMPLE 21

A copolymer was made by repeating exactly the process described in Example 1 except that 0.2 parts dodecanthiol were used. The resultant copolymer powder was then formed into a powdered zinc salt in the same manner, and using the same materials and amounts of materials, as described in Example 15. The resultant product was termed product Y.

It will be appreciated that due to the decreased amount of dodecanthiol the molecular weight of product Y is higher than the molecular weight of product X.

EXAMPLE 22

This example shows the influence of molecular weight on the performance of polymers of the invention and compared to the properties of product X, of Example 15, and product Y, of Example 21. In this example solutions containing various amounts of product X or product Y and containing also a weed-killer, namely Atrazine or Cotoran were sprayed onto soil which was then irregated to an extent equivalent to 500 m³/ha. Results on sandy soil are given in Table I and the results on clay soil are given in Table 2. It will be seen that the use of products X and Y, and in particular the use of the high molecular weight product, namely Y, significantly reduces the depth to which the weed-killer is leached. Accordingly the weedkiller is maintained nearer the surface of the soil and so is effective against surface rooting weeds but ineffective against deep rooting crops.

Table 1

| Weedkiller | Product | Concentration of Product | Depth of Weedkiller Leaching (cm) |
| --- | --- | --- | --- |
| Atrazine | — | — | 16 |
| Atrazine | Y | 0.75 | 14 |
| Atrazine | Y | 1.25 | 13 |
| Atrazine | Y | 2.00 | 10 |
| Atrazine | X | 2.50 | 14 |
| Cotoran | — | — | 17 |
| Cotoran | Y | 0.75 | 13 |
| Cotoran | Y | 1.25 | 11 |
| Cotoran | Y | 2.00 | 6 |
| Cotoran | X | 2.50 | 14 |

Table 2

| Weedkiller | Product | Concentration of Product | Depth of Weedkiller Leaching (cm) |
| --- | --- | --- | --- |
| Atrazine | — | — | 9 |
| " | Y | 2.00 | 4 |
| Cotoran | — | — | 11 |
| " | Y | 2.00 | 5 |

We have described in our copending Application 14848/71, filed 13th May 1971, hydrophilic copolymers derived by bulk polymerisation from a monomer mixture comprising 25 to 50% by volume of lower alkyl acrylate or lower alkyl methacrylate, 40 to 60% by volume of acrylic acid or methacrylic acid and 5 to 20% by volume of a long chain ester of acrylic acid or methacrylic acid and in which copolymer the acid groups are neutralised. In practice complete neutralisation of the acid groups was effected. As a result of the copolymers having been made by bulk polymerisation they generally had a high molecular weight.

I claim:

1. In an agricultural fine chemical composition, the improvement which comprises employing as the copolymeric carrier from a film of which an effective amount of the agricultural fine chemical is releasable: a copolymer derived from a monomer mixture selected from the class consisting of acrylic acid, from 20 to 70 parts of at least one member selected from the class consisting of lower alkyl acrylates and lower alkyl methacrylates, and from 5 to 20 parts of a long chain ester of acrylic acid or methacrylic acid, where the chain length is from 8 to 18 carbon atoms in the ester portion, said copolymer having a molecular weight of more than one million as determined by its intrinsic viscosity in methylethyl ketone at 25° C, in which at least some of the acid groups have been neutralized by multivalent inorganic cations selected from the class consisting of zinc and copper.

2. The composition of claim 1 wherein the agricultural fine chemical is a herbicide.

3. An aqueous solution of the material of claim 1.

4. A method for releasing an effective amount of an agricultural fine chemical to a locus at a controlled rate comprising:

a. applying to the locus a solution or dispersion of the chemical to be released in an aqueous solution of a copolymer derived from a monomer mixture comprising from 20 to 60 parts of a member selected from the class consisting of acrylic acid and methacrylic acid, from 20 to 70 parts of a member selected from the class consisting of lower alkyl acrylates and lower alkyl methacrylates, and from 5 to 20 parts of a long chain ester of acrylic or methacrylic acid, where the long chain has from 8 to 18 carbon atoms, said copolymer having a molecular weight of more than the million as determined by its intrinsic viscosity in methylethyl ketone at 25° C, in which at least some of the acid groups have been neutralized by multivalent inorganic cations selected from the class consisting of zinc and copper; and b. allowing the water to evaporate from the solution.

5. The method of claim 4 wherein the copolymer has been bulk copolymerised.

* * * * *